United States Patent [19]

Kaltenbronn et al.

[11] Patent Number: 4,681,972

[45] Date of Patent: Jul. 21, 1987

[54] SEPARATION OF DIASTEREOMERS

[75] Inventors: James S. Kaltenbronn; Michael A. Stier, both of Ann Arbor, Mich.

[73] Assignee: Warner-Lambert Company, Morris Plains, N.J.

[21] Appl. No.: 908,438

[22] Filed: Sep. 16, 1986

[51] Int. Cl.[4] ............................................. C07B 57/00
[52] U.S. Cl. ...................................... 560/29; 560/115
[58] Field of Search ................. 560/29, 115; 562/401, 562/402

[56] References Cited

U.S. PATENT DOCUMENTS 3,887,615  6/1975  Keith et al. ...................... 562/401 X
4,240,975 12/1980  Umezawa et al. ................ 560/29 X
4,391,986  7/1983  Umezawa et al. ................ 560/29 X

*Primary Examiner*—Michael L. Shippen
*Attorney, Agent, or Firm*—Elizabeth M. Anderson

[57] ABSTRACT

The S,S-isomers of Boc-benztine and Boc-cyclotine can be produced via the fractional crystallization of R-(+)-alpha-methylbenzylamine salt(s). The products are useful in the production of renin inhibitors.

3 Claims, No Drawings

SEPARATION OF DIASTEREOMERS

BACKGROUND

Statine, i.e., 4-amino-3-hydroxy-6-methylheptanoic acid, is an amino acid present in pepstatin, which is known to be an important fragment in certain renin inhibitors. Closely related to statine are certain substituted 4-amino-3-hydroxy-pentanoic acids. These acids are currently of interest in the preparation of renin inhibitors. Two publications concerning these pentanoic acid analogs are: D. H. Rich and E. T. O. Sun, *J. Med. Chem.* 23, 27 (1980) and J. A. Boger and D. F. Veber, U.S. Pat. No. 4,485,099 (1984), the disclosures of which are hereby incorporated by reference.

The compounds, N-(tert.-butoxycarbonyl)-4(S)-amino-3(S)-hydroxy-5-phenylpentanoic acid (hereafter "S,S-Boc-benztine") and N-(tert.-butoxycarbonyl)-4(S)-amino-3(S)-hydroxy-5-cyclohexanepentanoic acid (hereafter "S,S-Boc-cyclotine") are components of renin inhibitors. The separation of the S,S-isomers from mixtures of diastereomers containing them can be effected by column chromatography of their esters on a small scale. However, a technique useful for the large scale recovery of these compounds is desirable.

This application is related to U.S. Ser. No. 735,933, filed May 20, 1985, now U.S. Pat. No. 4,650,897, which deals with the separation of certain Boc-statine isomers.

THE INVENTION

It has been discovered that the S,S-isomer of Boc-benztine can be separated from diastereomeric mixtures which contain it and other isomers by fractional crystallization of the R-(+)-alpha-methylbenzylamine salt. Subsequently, the S,S Boc-benztine can be catalytically hydrogenated to the S,S-isomer of Boc-cyclotine.

In addition, Boc-cyclotine's S,S-isomer can be separated from appropriate mixtures of diastereomers by fractional crystallization of one or more suitable amine salts.

ADVANTAGES

The invention has as its principal advantage the fact that large scale production of Boc-benztine and/or Boc-cyclotine can be carried out efficiently.

Other aspects and advantages of the invention will be apparent upon consideration of the following description.

DESCRIPTION OF THE INVENTION

The invention is concerned with a method for separating certain substituted 4-amino-3-hydroxypentanoic acids.

Specifically, it deals with the recovery of what applicants call Boc-benztine (or N-tertiary-butoxycarbonyl)-4(S)-amino-3-(S)-hydroxy-5-phenylpentanoic acid,

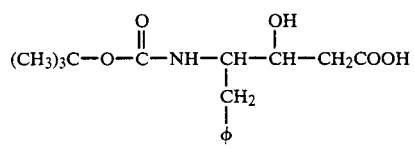

(wherein φ is phenyl) and the compound applicants call Boc-cyclotine (or N(tert-butoxycarbonyl)-4-(S)-amino-3-(S)-hydroxy-5-cyclohexanepentanoic acid, which has formula II

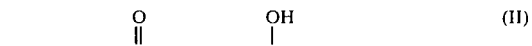

(wherein

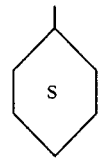

is cyclohexyl).

T pre red separation process of the invention involves (1) production of the R-(+)-alpha-methylbenzylamine salt of the Boc-benztine or Boc-cyclotine, (2) one or more fractional crystallization(s) of the salt from solution to produce solid crystals in which the S,S-isomers predominate and (3) regeneration of the acid.

The starting material from which the amine salts are produced may be Boc-benztine or Boc-cyclotine or functionally eguivalent analogs thereof.

The Boc-containing reactant is contacted under suitable reaction conditions with at least one amine species which functions to assist in the production of crystals which contain a predominant amount of the S,S-isomer of the amine salt(s)—i.e., the concentration of S,S-isomer is greater than that of other isomer(s) present. One preferred group of amines includes R-(+)-alpha-methylbenzylamine and functional equivalents thereof. Other amines contemplated for use in the invention include R-(+)-1-(1-naphthyl)-ethylamine, and the like.

When the amine salt formation is substantially complete, crystallization occurs. The crystallization takes place from solution using ethyl acetate/methanol, ethyl acetate/ethanol, ethyl acetate/isopropanol and/or other suitable solvent(s) or diluent(s). The solvents or other diluents used during the crystallization step(s) can also be employed during the previous salt formation and the subsequent regeneration of the acid and/or other recovery operation(s).

The initial solution crystallization is followed by one or more recrystallization(s) to optimize the concentration of S,S-isomer in the precipitated or crystallized solid particles. Generally, from about one to about 4 additional recrystallizations are employed, with a total of about two crystallizations preferred.

During the crystallization steps the temperature and pressure will vary depending upon parameters such as starting materials, solvents, relative humidity, solvent quantity, instrumentation and the like.

. Unless set out otherwise, all temperatures stated herein are in degrees Celsius.

The recovery process can be stopped with the recrystallization and isolation of the amine salt(s). However, it is generally preferred that the amine salt be converted to the free acid of Boc-benztine or Boc-cyclotine before recovery of the acid is effected.

The regeneration of the free acid from the amine salt takes place under conditions well known in the art. Generally, the amine salt suspended in an organic solvent, is contacted with a suitable acid at a low temperature i.e., room temperature or less, preferably about 1° to about 10°. A wash with sodium chloride solution follows. The product is then dried, over MgSO₄ and the solvent/diluent removed with the optional use of reduced pressure.

When Boc-benztine is the acid product, it can be converted to Boc-cyclotine via conventional hydrogenation. Generally, catalytic hydrogenation using, e.g., a rhodium on carbon catalyst and one or more solvent(s) is preferred.

When the requisite hydrogenation has occurred, the reaction is terminated and the reaction liquid filtered to remove the catalyst.

The Boc-cyclotine can then be recovered via removal of any solvent or other diluent. Such removal may be by solvent/diluent evaporation or stripping under reduced pressure. The resultant white material, which is foamy, contains a predominant quantity of Boc-cyclotine.

EXAMPLE

The following example further illustrates the invention:

N-(tert.-Butoxycarbonyl)-4(S)-amino-3(R,S)-hydroxy-5-phenylpentanoic Acid. Ethyl Ester A solution of 92.4 ml (0.706 moles) of diisopropylamine in 600 ml of tetrahydrofuran was cooled to −35° and 271.1 ml (0.706 moles) of a 2.6M solution of n-butyl lithium in heptane was added slowly. The solution was then cooled to −85° in an ethanol/liquid nitrogen bath and 68.9 g (0.706 moles) of ethyl acetate was added slowly keeping the reaction temperature below −80°. After stirring for 15 minutes, a solution of 125.5 g (0.504 moles) of Boc-phenylalaninal [J. A. Fehrentz and B. Castro, *Synthesis,* 676 (1983).] in 1 L. of tetrahydrofuran, precooled to −78°, was added dropwise, keeping the temperature below −80°. After stirring at −80° for 15 minutes, the solution was allowed to warm to −5° and 400 ml of 12% hydrochloric acid was added. The pH was adjusted to 2.0 and the solution extracted twice with ether. The combined ether solution was washed with 1N hydrochloric acid, water, saturated sodium bicarbonate, and then with saturated sodium chloride solution. After drying over magnesium sulfate the ether was removed under reduced pressure to give 154 g. (90.6% yield) of the crude product as a white solid sufficiently pure for use in the next step.

The product has been previously described. See D. H. Rich and E. T. O. Sun, *J. Med. Chem.* 23, 27 (1980).

N-(tert.-Butoxycarbonyl)-4(S)-amino-3(R,S)-hydroxy-5-phenylpentanoic Acid

Partial Separation of Diastereomers

A suspension of 154 g (0.456 moles) of crude N-tert-butoxycarbonyl)-4(S)-amino-3(R,S)-hydroxy-5-phenylpentanoic acid, ethyl ester in 1 L. of a 1:1 dioxane/water mixture was brought to pH 12 using a 50% solution of sodium hydroxide and maintained at this pH with additions of sodium hydroxide, monitoring the reaction with a pH meter standardized with a 1:1 mixture of pH 10 buffer/dioxane. The suspended solid soon went into solution. and the solution was kept at pH 12 for two hours. The pH was then brought to 7.0 with dil. HCl and the solution washed with ether. The pH was then brought to 1.8 and the precipitated product collected. There was obtained 68 g of the crude acid. HPLC analysis showed this to be a mixture of 36% S,S-isomer and 64% of the S,R-isomer.

The solid was suspended in 2.8 L. of ether and stirred overnight. The undissolved solid was collected to give 42.5 g of material. HPLC analysis showed this to be 5.2% S,S-isomer and 94.8% S,R-isomer. The filtrate was concentrated under reduced pressure to give 24.3 g of a white solid. HPLC analysis showed there to be 87.9% of the S,S-isomer and 12.1% of the R,S-isomer.

The filtrate from the original acid precipitation was extracted three times with ether, the combined ether extracts dried over magnesium sulfate, and the solvent removed under reduced pressure to give 31.5 g of a white solid. HPLC analysis of this material showed 75.8% S,S-isomer and 24.2% S,R-isomer. This material was suspended in 1.26 L. of ether and stirred overnight. The undissolved solid was collected to give 12.3 g of material. HPLC analysis showed 51.5% S,S-isomer and 48.5% S,R-isomer. The filtrate was concentrated to give 18.8 g of a solid. HPLC analysis of this material showed 90.1% S,S-isomer and 9.9% S,R-isomer.

After resuspending the 12.3 g of material from above (51.5% S,S-isomer) in 490 ml of ether, stirring overnight, filtering off the insoluble material, and concentrating the filtrate under reduced pressure, there was obtained an additional 6.0 g of material with an isomer ratio of 87.2% S,S-isomer and 12.8% S,R-isomer.

Combining all the fractions enriched in the S,S-isomer gave 49.1 g of product with an isomer ratio of 88.6% S,S-isomer and 11.4% S,R-isomer.

SALT FORMATION AND FRACTIONAL CRYSTALLIZATION

A solution of 22.45 g (0.0726 moles) of N-(tert-butoxycarbonyl)-4(S)-amino-3-(R,S)-hydroxy-5-phenylpentanoic acid (88.6% S,S-isomer) in 100 ml of methanol was treated with 9.6 ml (0.0726 moles) of R-(+)-alpha-methylbenzylamine and diluted with 650 ml of ethyl acetate. Crystallization soon occurred and the mixture was kept at 5° overnight. The precipitated salt was collected and washed with ethyl acetate. There was obtained 21.0 g of a white solid, mp 169°–175°; $[\alpha]_D^{23}$ −24.5° (c, 0.6. methanol).

A small sample was used to regenerate the free acid. HPLC analysis showed 92.2% S,S-isomer and 7.8% S,R-isomer.

SECOND RECRYSTALLIZATION

A solution of 21.0 g of the above salt was dissolved in 100 ml of warm methanol and diluted with 500 ml of ethyl acetate. Crystallization soon occurred and the mixture was kept at 5° overnight. The precipitated salt was collected and washed with ethyl acetate. There was obtained 13.9 g of a white solid, mp 176°–178°, $[\alpha]_D^{23}$ −27.9 (c, 0.56, methanol).

A small sample was used to regenerate the free acid. HPLC analysis showed 97.8% S,S-isomer and 2.2% S,R-isomer.

Regeneration of Free Acid From the Salt to yield N-(tert.-butoxycarbonyl)-4(S)-amino-3(S)-hydroxy-5-phenylpentanoic Acid.

A suspension of 14.7 g of the above salt in 500 ml of ethyl acetate was washed with two 100 ml portions of cold 1N HCl, then with sat. sodium chloride. After drying over magnesium sulfate and removal of the solvent under reduced pressure, there was obtained 10.16 g of a white solid, mp 146°–148°, $[\alpha]_D^{23}$ −34.1 (c, 1.05, methanol). HPLC analysis showed 98.3% S,S-isomer and 1.7% S,R-isomer.

N-(tert.-Butoxycarbonyl)-4(S)-amino-3(S)-hydroxy-5-cyclohexanepentanoic Acid.

A solution of 16.49 g of N-(tert-butoxycarbonyl)-4(S)-amino-3(S)-hydroxy-5-phenylpentanoic acid in 150 ml of isopropyl alcohol was reduced at 24°, 50 p.s.i. using 1.5 g of 10% rhodium on carbon as the catalyst. When the required amount of hydrogen had been taken up, the reaction was stopped and the mixture filtered to remove the catalyst. Removal of the solvent under reduced pressure gave 16.9 g of the product as a white foam. $[\alpha]_D^{23}$ −29.1° (c, 1.06, methanol).

Reasonable variations, such as those which would occur to a skilled artisan, can be made herein without departing from the scope of the invention.

We claim:

1. A process for separating S,S-isomers of Boc-benztine or Boc-cyclotine from diastereomeric mixtures thereof which comprises the steps of:
   (1) contacting the mixture with the R-(+) alpha-methylbenzylamine or R-(+)-1-(1-naphthyl)-ethylamine to produce a salt,
   (2) fractionally crystallizing from an acetate/alcohol solution one or more times to yield crystals in which the S,S-isomer predominates, and
   (3) regenerating the acid.
2. The process of claim 1 in which the starting mixture contains diastereomers of Boc-benztine.
3. The process of claim 2 which includes the additional step of:
   (4) hydrogenating catalytically the product of step (3) to produce Boc-cyclotine.

* * * * *